United States Patent [19]

Ostroff

[11] Patent Number: 5,215,081

[45] Date of Patent: Jun. 1, 1993

[54] METHOD AND DEVICE FOR MEASURING SUBTHRESHOLD DEFIBRILLATION ELECTRODE RESISTANCE AND PROVIDING A CONSTANT ENERGY SHOCK DELIVERY

[75] Inventor: Alan H. Ostroff, Philadelphia, Pa.

[73] Assignee: Telectronics Pacing Systems, Inc., Englewood, Colo.

[21] Appl. No.: 628,700

[22] Filed: Dec. 14, 1990

[30] Foreign Application Priority Data

Dec. 28, 1989 [AU] Australia ............... PJ8039

[51] Int. Cl.$^5$ ............................... A61N 1/39
[52] U.S. Cl. ................... 128/419 D; 128/734
[58] Field of Search ........... 128/419 PT, 419 PG, 128/419 D, 723, 734

[56] References Cited

U.S. PATENT DOCUMENTS

| | | | |
|---|---|---|---|
| 3,713,449 | 1/1973 | Mulier | 128/419 PG |
| 4,328,808 | 5/1982 | Charbonnier et al. | 128/419 D |
| 4,574,810 | 3/1986 | Lerman | 128/419 D |
| 4,596,252 | 6/1986 | Nelson | 128/419 PG |
| 4,630,615 | 12/1986 | Yomtov | 128/734 |
| 4,694,830 | 9/1987 | Lekholm | 128/419 PG |
| 4,697,591 | 10/1987 | Lekholm et al. | 128/419 PG |
| 4,721,110 | 1/1988 | Lampadius | 128/419 PG |
| 4,771,781 | 9/1988 | Lerman | 128/419 D |
| 4,869,252 | 9/1989 | Gilli | 128/419 PG |
| 4,870,341 | 9/1989 | Pihl et al. | 324/57 R |

FOREIGN PATENT DOCUMENTS

| | | | |
|---|---|---|---|
| 0315368 | 5/1989 | European Pat. Off. | 1/39 |
| 2712352 | 9/1978 | Fed. Rep. of Germany | 1/38 |

OTHER PUBLICATIONS

R. E. Kerber et al., "Automated Impedance-Based Adjustment for Defibrillation: Experimental Studies," *Circulation*, vol. 71, No. 1, pp. 136–140 (Jan. 1985).

J. H. Lawrence et al., "The Characterization of Human Transmyocardial Impedance During Implantation of the Automatic Internal Cardioverter Defibrillator," *PACE*, vol. 9, pp. 745–755 (Sep.–Oct. 1986).

W. A. Tacker, Jr. et al., "Electrical Defibrillation," appearing at p. 14 of W. A. Tacker, Jr. et al.'s book *Electrical Defibrillation*, published by the CRC Press, Inc. of Boca Raton, Fla. (1980).

L. A. Geddes et al., "The Prediction of the Impedance of the Thorax to Defibrillating Current," *Medical Instrumentation*, vol. 10, No. 3, pp. 159–162 (May–Jun. 1976).

G. V. Savino et al., "Transventricular Impedance During Fibrillation," *IEEE Transactions on Biomedical Engineering*, vol. BME-30, No. 6, pp. 364–367, (Jun. 1983).

R. E. Kerber et al., "Advance Prediction of Transthoracic Impedance in Human Defibrillation and Cardioversion: Importance of Impedance in Determining the Success of Low-Energy Shocks," *Circulation*, vol. 70, No. 2, pp. 303–308 (Aug. 1984).

*Primary Examiner*—Kyle L. Howell
*Assistant Examiner*—Kennedy J. Schaetzle
*Attorney, Agent, or Firm*—Gottlieb, Rackman & Reisman

[57] ABSTRACT

A method and apparatus for measuring subthreshold defibrillation electrode resistance are disclosed. A known subthreshold current pulse is sourced across the electrodes, the resulting voltage is measured and the electrode resistance is calculated from these values. The calculated electrode resistance may be utilized to adjust the energy level of a defibrillation shock used to treat a detected tachyarrhythmia. In one embodiment the calculated resistance and a predetermined leading edge voltage are used to calculate and adjust the duration of the defibrillation shock. In another embodiment the calculated electrode resistance and a predetermined shock duration are used to adjust the leading edge voltage of the defibrillation shock.

47 Claims, 4 Drawing Sheets

STEP 1: END OF 10 MICROSECOND PULSE $T_1$, AT B
$$V_C = V_{NOISE} - I_1 \times R_{DEFIB}$$

STEP 2: END OF 10 MICROSECOND PULSE $T_2$, AT D
$$V_S = I_1 \times R_{DEFIB}$$

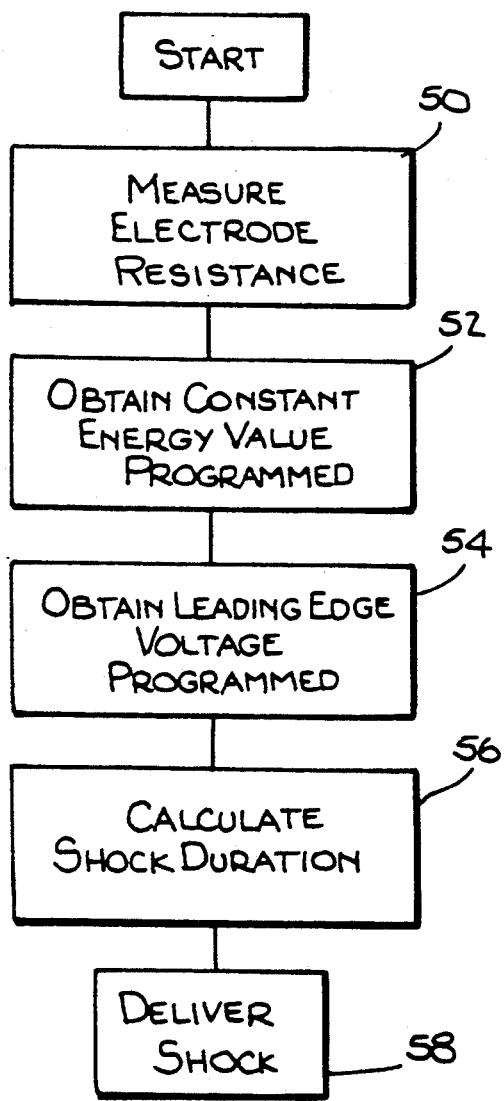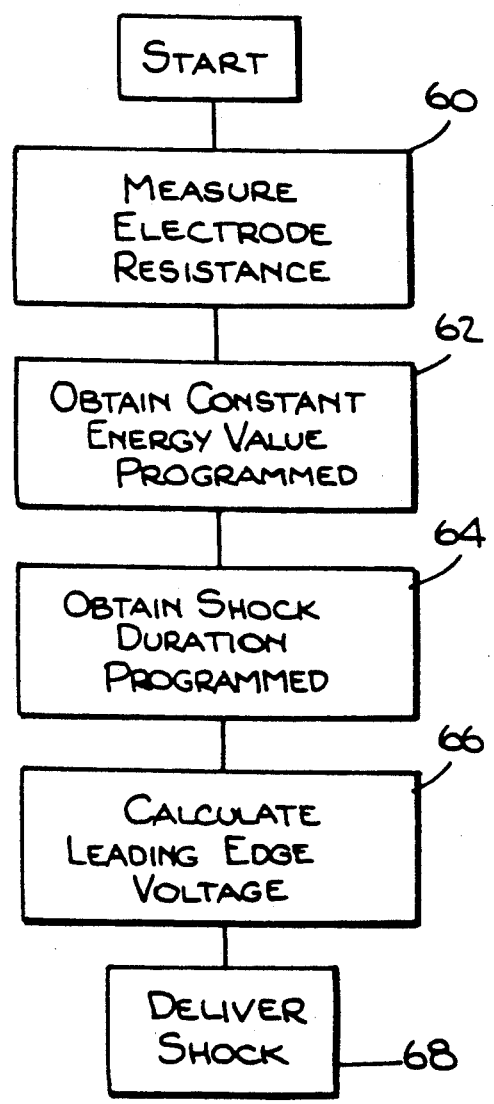
Fig. 4A.
Fig. 4B.

METHOD AND DEVICE FOR MEASURING SUBTHRESHOLD DEFIBRILLATION ELECTRODE RESISTANCE AND PROVIDING A CONSTANT ENERGY SHOCK DELIVERY

BACKGROUND OF THE INVENTION

This invention relates to a method and device for measuring defibrillation electrode resistance, and, more particularly, to such a method and device which employs a subthreshold current pulse, rather than a defibrillation shock, in connection with the measurement in order to avoid unnecessary stimulation of the patient's heart. The method may be used in either an implantable or an external defibrillating device.

The measurement of defibrillation electrode resistance is an important parameter in the field of defibrillation and especially during the process of implantation of implantable defibrillators. Knowledge of the defibrillation electrode resistance parameter has an additional advantage, subsequent to implantation and prior to the application of defibrillation therapy, following the detection of a tachyarrhythmia requiring therapy. Measured electrode resistance variations furnish useful information regarding electrode integrity and positioning. Comparisons may also be made to previous measurements to provide a parameter for the control of defibrillation threshold tracking. Another important advantage of the resistance measurement is to provide a means of maintaining a constant-energy defibrillation shock delivery system in implantable defibrillators.

A very useful application of defibrillation electrode resistance measurement at implantation is to verify the integrity and correct positioning of the defibrillation electrode connections prior to inducing tachycardia and subsequently delivering a defibrillation shock to revert the patient's rhythm. However, present methods are either unsuitable for implantable defibrillators, or they require a shock to be delivered, thus increasing the risk to the patient in the event that a successful reversion does not occur.

U.S. Pat. No. 4,574,810 to B. B. Lerman describes an external defibrillator which relies on low amplitude sinusoidal current to automatically ascertain the transthoracic resistance of a patient and then automatically apply a defibrillation shock according to the transthoracic resistance and an amperes per ohm factor. The use of a sinusoidal current, rather than a pulse, and the use of complicated and bulky circuitry make this device inappropriate for implantable defibrillators.

In an article entitled "Automated Impedance-Based Energy Adjustment for Defibrillation: Experimental Studies," by Kerber et al., in *Circulation*, Vol. 71, No. 1, pp. 136-140 (1985), it is shown how transthoracic impedance was predicted in advance of the first shock by passing a low level current between the defibrillator electrodes during the defibrillator charge cycle. This impedance prediction technique was described earlier by Geddes et al. in an article entitled "The Prediction of the Impedance of the Thorax to Defibrillating Current," in *Medical Instrumentation*, Vol. 10, No. 3, (May-June 1976). This method has an application to external devices, and is very complicated and difficult to administer in external defibrillators, with even greater difficulty in implantable devices. This method is time consuming and non-instantaneous and requires a continuous application of low level current.

The same method is further described in an article by Kerber et al., entitled "Advance Prediction of Transthoracic Impedance in Human Defibrillation and Cardioversion: Importance of Impedance in Determining the Success of Low-Energy Shocks," *Circulation*. Vol. 70, No. 2, pp. 303-308 (1984). The method requires a measurement circuit which uses a high frequency signal of 31 kHz passing through the patient via paddles. The high frequency signal flows during the defibrillator charge cycle. Although this method is unsuitable for implantable defibrillators and is unable to achieve the purposes of the presently disclosed invention, the article highlights to a certain degree the importance of accurately predicting transthoracic impedance, in advance, in the field of external defibrillation.

An article in *IEEE Transactions on Biomedical Engineering*, Vol. BME - 30, No. 6, pp. 364-367 (June 1983), by Savino et al., entitled "Transventricular Impedance During Fibrillation," refers to the two methods of impedance measurements currently used as being (1) the injecting of a low constant sinusoidal current, and (2) the determination of the time constant of an exponential defibrillatory discharge. This article also states that for all practical purposes, the impedance load between the electrodes and the heart may be considered as resistive.

By providing an instantaneous subthreshold measurement of defibrillation electrode resistance, the integrity of the electrode system in an implantable defibrillator can be established accurately prior to delivering a defibrillation shock, both at implantation and at the time of standard therapy to a patient having an implantable device. This is performed without any unnecessary stimulation of the patient's heart, thereby ensuring a high level of safety to the patient.

Also, with respect to another aspect of the invention, present constant energy defibrillation shock delivery systems, such as the system used by Cardiac Pacemaker Inc. (CPI) in their implantable defibrillator, maintain a constant energy defibrillation shock by varying the duration of the defibrillation shock. It is known mathematically that the amount of energy delivered is a function of the leading and trailing edge voltage of a truncated exponential wave-form. In the CPI implantable defibrillator, the trailing edge voltage is monitored, and when the desired trailing edge voltage is reached, the pulse is truncated.

The problem with this approach is that large shock durations result in non-optimal defibrillation thresholds. The defibrillation strength-duration curve during defibrillation exhibits a "U"-shape for a delivered energy. This is described by Tacker and Geddes at page 14 of "Electrical Defibrillation," published in 1980 by CRC Press of Boca Raton, Fla. As a result of this "U"-shaped curve, an optimum value for minimizing delivered energy can be chosen. Thus, any decreasing or increasing of the shock duration from this optimum value or "minimum energy point" will result in increased defibrillation thresholds.

Accordingly, it is desirable to use an improved constant energy algorithm which is based on the performing of a subthreshold defibrillation electrode resistance measurement prior to delivering a defibrillation shock.

It is, therefore, a primary object of the invention to ensure the integrity of defibrillation electrodes prior to delivering a defibrillation shock to a patient.

It is a further object of the invention to perform a defibrillation electrode resistance measurement using a subthreshold technique which will not affect the electrical timing of the heart and thereby reduces the risk to the patient.

It is another object of the invention to perform a simple and substantially instantaneous measurement of defibrillation electrode resistance.

It is a still further object of the invention to selectively obtain either a single measurement, such as prior to the delivery of a defibrillation shock, or to continually take measurements at preprogrammed intervals.

It is yet another object of the invention to provide for and control an improved constant-energy delivery system in an implantable defibrillator.

It is an additional object of the invention to provide a parameter for the control of defibrillation threshold tracking.

Further objects and advantages of this invention will become apparent as the following description proceeds.

SUMMARY OF THE INVENTION

Briefly stated, and in accordance with one embodiment of this invention, there is provided a method of measuring subthreshold defibrillation electrode resistance, comprising the steps of sourcing a single subthreshold current pulse across the electrodes and then measuring the resulting voltage. The method may be utilized in an implantable defibrillating device, subsequent to implantation of the device and/or the electrodes for the device and prior to the delivery of a defibrillation shock by the device. Alternatively, it may be utilized in such a device at a time subsequent to the detection of a tachyarrhythmia and prior to the delivery of a defibrillation shock to revert the tachyarrhythmia.

In accordance with another aspect of the invention, there is provided a constant energy defibrillation shock delivery method for a defibrillating device having two or more defibrillating electrodes and an electrode resistance measuring circuit. This method includes the steps of detecting a tachyarrhythmia, switching the electrode connections to the resistance measuring circuit, sourcing a single subthreshold current pulse from the resistance measuring circuit, measuring the resulting voltage, calculating the electrode resistance from the measured voltage and the current pulse magnitude, using the calculated electrode resistance to adjust the energy level of the defibrillation shock, and delivering a defibrillation shock to treat the detected tachyarrhythmia. As a further feature of the invention, this method contemplates that the calculated electrode resistance and a predetermined leading edge voltage may be used to calculate and adjust the duration of the defibrillation shock. Alternatively, the calculated electrode resistance and a predetermined shock duration may be used to adjust the leading edge voltage of the defibrillation shock.

In accordance with a further aspect of the invention, the method provides a parameter for the control of defibrillation threshold tracking in a defibrillating device having two or more defibrillating electrodes and an electrode resistance measuring circuit. This method includes the steps of detecting a tachyarrhythmia, switching the electrode connections to the resistance measuring circuit, sourcing a single subthreshold current pulse from the resistance measuring circuit, measuring the resulting voltage, calculating the electrode resistance from the measured voltage and the magnitude of the current pulse, comparing the calculated electrode resistance with the last measured value, adjusting the energy level of the defibrillation shock to the maximum value if the last measured value of electrode resistance is exceeded by a specified amount, and delivering the maximum defibrillation shock to treat the detected tachyarrhythmia.

The invention also encompasses defibrillation devices constructed and arranged to operate in accordance with the foregoing method features.

BRIEF DESCRIPTION OF THE DRAWINGS

While the specification concludes with claims particularly pointing out and distinctly claiming the subject matter of this invention, it is believed that the invention will be better understood from the following description, taken in conjunction with the accompanying drawings, in which:

FIGS. 4A and 4B are respective flow charts of first and second algorithms that may employed to deliver constant energy defibrillation shocks in accordance with the present invention.

DESCRIPTION OF THE PREFERRED EMBODIMENTS

Figure 1:
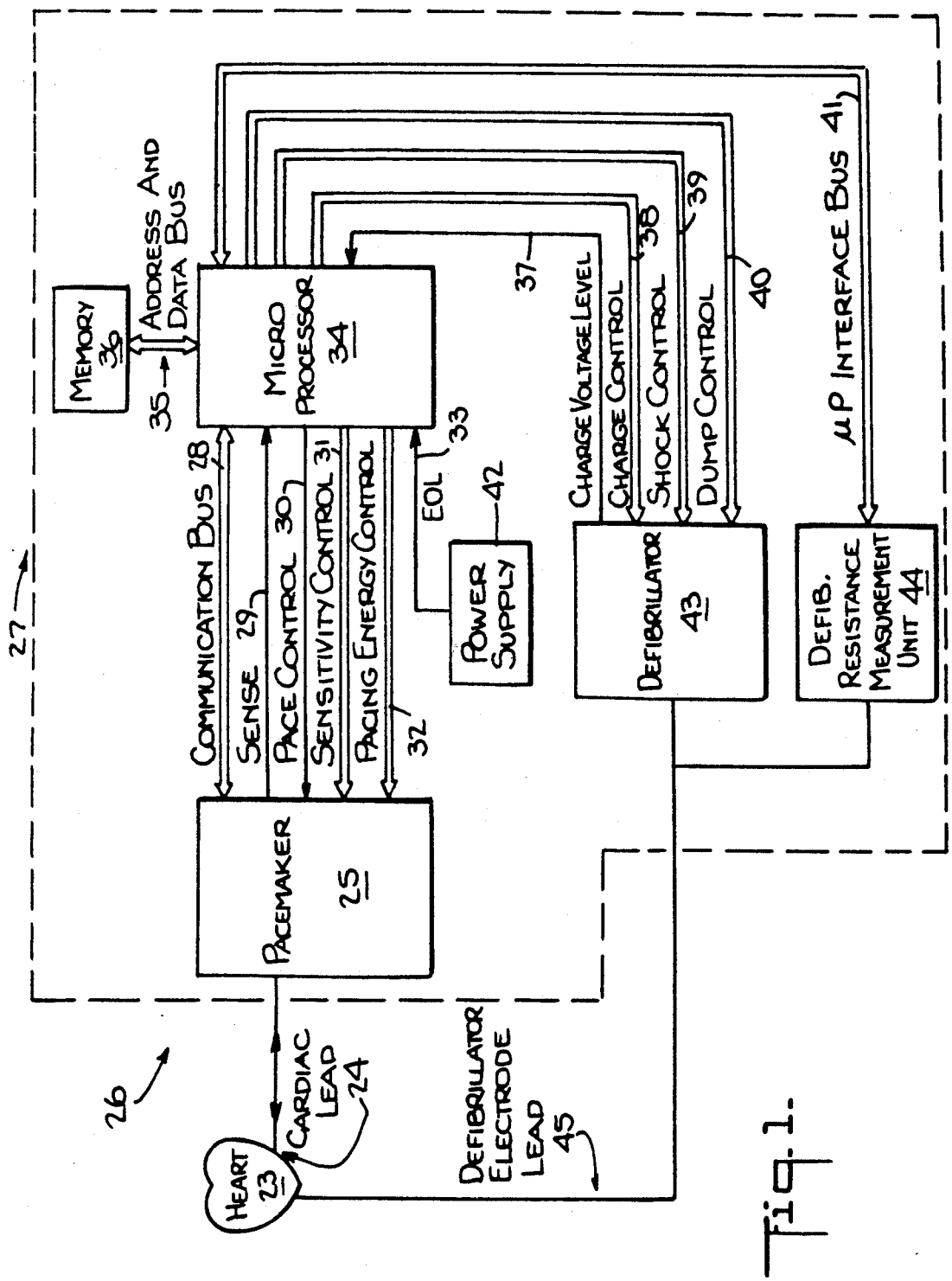
FIG. 1 depicts a block diagram of an arrhythmia control system in which the present invention is incorporated.

Referring to FIG. 1, there is depicted a block diagram of an arrhythmia control system 26 which may be utilized in either a single chamber implantable arrhythmia control device, as shown, or in a dual chamber device. An implantable single chamber antitachycardia pacing, bradycardia pacing, defibrillating or cardioverting arrhythmia control device of the type shown in FIG. 1 is disclosed in greater detail in the U.S. Pat. No. 4,869,252 of Norma Louise Gilli, dated Sep. 26, 1989, entitled "Apparatus and Method for Controlling Pulse Energy in Antitachyarrhythmia and Bradycardia Devices," which is assigned to the assignee of the present invention and is incorporated herein by reference. An implantable dual chamber antitachycardia pacing, bradycardia pacing, defibrillating or cardioverting arrhythmia control device is disclosed in the copending U.S. patent application Ser. No. 462,499 of Norma Louise Gilli, filed Jan. 5, 1990, entitled "Apparatus and Method For Antitachycardia Pacing In Dual Chamber Arrhythmia Control System," now U.S. Pat. No. 4,998,974 which is assigned to the assignee of the present invention and is incorporated herein by reference.

System 26 is preferably designed to be implantable, and includes a pulse module 27 and appropriate leads for connecting module 27 to a patient's heart 23. More particularly, system 26 includes a cardiac lead 24 extending to the atrium of a patient's heart 23 for the administration of therapy to the atrium and/or extending to the ventricle of a patient's heart for the administration of therapy to the ventricle. System 26 generally also includes a pacemaker 25 for the detection of analog signals representing cardiac electrical activity, and for the delivery of pacing pulses to the heart; a microprocessor 34 which, in response to various inputs received from the pacemaker 25 as well as from a defibrillator 43, performs various operations so as to generate different control and data outputs to both pacemaker 25 and defibrillator 43; and a power supply 42 for the provision of a reliable voltage level to pacemaker 25, microprocessor 34 and defibrillator 43 by suitable electrical conductors (not shown). Defibrillator 43 produces a high voltage to charge its capacitors (not shown) and then discharges them in response to control signals from microprocessor 34. A defibrillator electrode lead 45 transfers the energy of a defibrillator shock from the implanted pulse module 27 to the surface of the heart 23.

Microprocessor 34 is connected to an external memory 36 by an address and data bus 35. An end-of-life (EOL) signal line 33 is used to provide, to microprocessor 34, a logic signal indicative of the approach of battery failure in power supply 42.

The microprocessor 34 and pacemaker 25 are connected by a communication bus 28, a sense line 29, a pace control line 30, a sensitivity control bus 31, and a pacing energy control bus 32. Furthermore, the microprocessor 34 is connected to defibrillator 43 by a charge voltage level line 37, a charge control bus 38, a shock control bus 39, and a dump control bus 40. A defibrillation resistance measurement unit or circuit 44 is connected to the defibrillator electrode lead 45 which connects to the heart 23. Additionally, the defibrillation resistance measurement unit 44 is connected to the microprocessor 34 by a microprocessor interface bus 41, as is more fully described below in connection with FIG. 2.

The energy of the defibrillation shock is determined by the leading edge voltage and the duration of the truncated exponential wave form, as indicated earlier. The microprocessor 34 controls both of these parameters by means of signals sent through the shock control bus 39, the charge control bus 38, and the charge voltage level line 37. The leading edge voltage is controlled by asserting the charge control signal via bus 38 and observing the charge voltage level signal in line 37 until the "target leading edge voltage" is reached. Microprocessor 34 also determines the duration of the shock by asserting the shock control signal via bus 39. Since both of these signals can be directly controlled by the microprocessor 34, the energy of a shock can be adjusted to remain constant by first measuring the patch resistance and then calculating the leading edge voltage for a fixed shock duration or, alternatively, by calculating the duration for a fixed leading edge voltage.

The following equation shows the relationships between leading edge voltage, shock duration, patch resistance, and the energy of a truncated exponential:

$$E = \tfrac{1}{2}CV^2[1 - e^{-2t/RC}]$$

Where:
t = shock duration
V = leading edge voltage
R = patch resistance
C = defibrillator capacitance, e.g., 150 microfarads.

Figure 2:
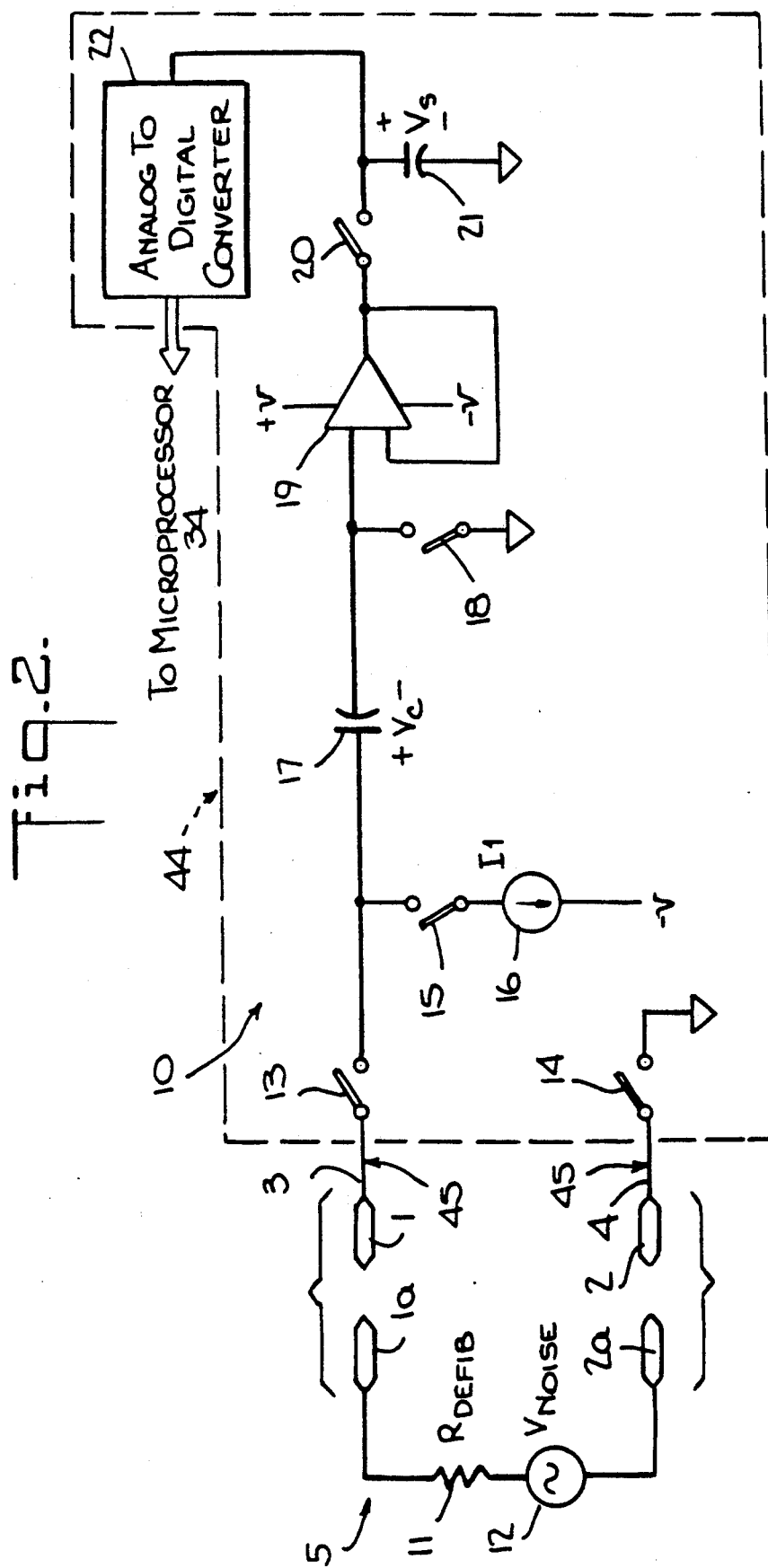
FIG. 2 depicts a resistance measurement circuit connected to a pair of defibrillator electrodes.

Referring to FIG. 2, there is shown a subthreshold electrode resistance measurement circuit 10 that is utilized in the defibrillation resistance measurement unit 44. The defibrillator electrodes are shown at 1 and 2. They are connected to the defibrillation resistance measurement unit 44 by leads 3 and 4 which, together, comprise the defibrillator electrode lead 45 of FIG. 1. The electrical effects stemming from the fact that the heart interconnects electrodes 1 and 2, and thus is connected to circuit 10, are shown generally in a circuit 5. The heart path between the defibrillation electrodes 1 and 2, which are identified at 1a and 2a, respectively, in the heart path circuit 5, includes both a resistance factor, representing the resistance of the heart tissue and the quality of the contacts which the electrodes 1 and 2 make with the heart tissue, and a noise factor, representing low frequency noise and electrode polarization artifacts. The resistance factor $R_{defib}$ of the heart and the defibrillator electrodes is shown at 11. The low frequency noise and electrode polarization voltage artifacts are represented by the voltage source 12 ($V_{noise}$) The low frequency noise is typically in the range of 50–60 Hz.

Circuit 10 contains five switches. Switch 13 and switch 14 are isolation switches which protect measurement circuit 10 during defibrillation. Switch 15 is a current source switch for a current source 16 (I1). Switch 18 is a subtract-and-hold switch. Switch 20 is a sample-and-hold switch. The operation of switches 18 and 20 is more fully described below.

Circuit 10 also includes a first capacitor 17 having a potential thereon of $V_c$, and a second capacitor 21 having thereon a potential of $V_s$. A buffer amplifier 19 is provided for accurate sampling of the voltages between the two capacitors 17 and 21. Buffer amplifier 19, switch 20 and capacitor 21 perform a sample-and-hold function.

An analog to digital converter 22 is provided in circuit with switch 20 and capacitor 21 of circuit 10. The analog to digital converter 22 and the sub-threshold electrode resistance measurement circuit 10 form part of the defibrillation resistance measurement unit 44 of FIG. 1, and are connected to the microprocessor 34 via the microprocessor interface bus 41.

Figure 3A:
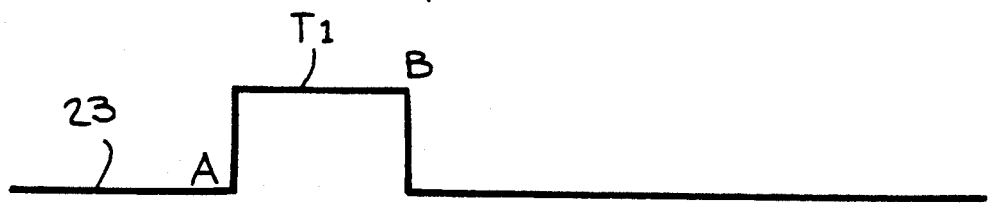
FIGS. 3A and 3B depict graphs of current vs. time for control signals applied to switches in the resistance measurement circuit of FIG. 2.
Figure 3B:
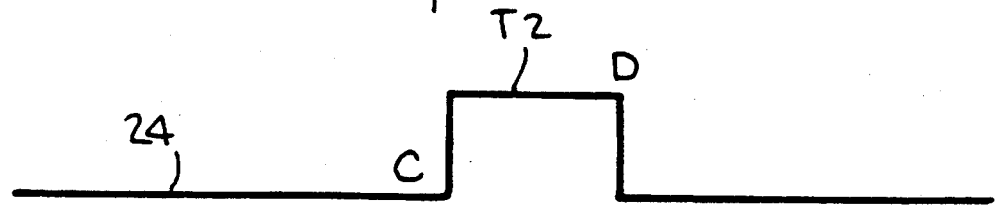

Referring to FIGS. 3A and 3B, the control signals for the analog switches of the measurement circuit 10 are there shown. As indicated in FIG. 3A, a 10 microsecond pulse T1 on signal wave 23, extending between points "A" and "B", serves as a control signal, producing a corresponding 10 microsecond current pulse of magnitude I1 from current source 16 (FIG. 2) when it is applied to close switches 15 and 18 while switches 13 and 14 are closed. Subsequently, immediately after pulse T1 ends at point "B" and opens switches 15 and 18, a 10 microsecond pulse T2 on signal wave 24, extending between points "C" and "D" as shown in FIG. 3B, is applied as a control signal to close switch 20 while switches 15 and 18 are open and switches 13 and 14 remain closed.

The basic principle of the measurement technique is to apply a subthreshold current pulse I1 from the current source 16 to the series combination of $R_{defib}$ resistance 11 and $V_{noise}$ voltage source 12. In this embodiment the preferred strength of the current pulse I1 is of the order of 2 milliamps. The next step in the procedure is to sample or store the resulting voltage $V_c$ across the series combination of $R_{defib}$ resistance 11 and $V_{noise}$ voltage source 12 once during the application of current pulse I1 on to capacitor 17. Then, after removing the current pulse I1, the voltage $V_s$ on capacitor 21 is sampled. This procedure provides a subtract-and-hold function and a rejection of low-frequency noise $V_{noise}$ from voltage source 12.

Switches 13 and 14 provide isolation between measurement circuit 10 and the resistance 11 of the defibrillation electrodes during defibrillation. The actual implementation of switches 13 and 14 is not important; either solid state devices or a mechanical relay may be used.

Switches 15, 18 and 20 are preferably solid state switches.

The defibrillation electrode impedance is modeled and confirmed clinically to be virtually a pure resistance, as shown in the article entitled "The characterization of Human Transmyocardial Impedance During Implantation of the Automatic Internal Cardioverter Defibrillator," by John H. Lawrence et al., in *PACE*, Vol. 9, (Sep.-Oct.) 1986. The $V_{noise}$ voltage source 12 is also shown to account for low-frequency noise and electrode polarization effects.

Referring now to FIGS. 3A and 3B in conjunction with the circuitry shown in FIG. 2, the operation of the measurement circuit is described the following two steps:

Step 1: Point "A" to Point "B": Switches 13, 14, 15 and 18 are closed, while switch 20 is in its open position. Assuming that the time constant of capacitor 17 and the resistance of switch 18 is much less than the period or duration of pulse T1, the voltage stored on capacitor 17 is $V_c = V_{noise} - I1 \times R_{defib}$.

Step 2: Point "C" to Point "D": Switches 13, 14 and 20 are closed, while switches 15 and 18 are in their open position. Assuming that the $V_{noise}$ voltage 12 does not change during step 2, the voltage stored on capacitor 21 is $V_s = I1 \times R_{defib}$.

The voltage $V_s$ on capacitor 21 is then sampled using analog to digital converter 22, having a suitable built in scale factor, to obtain the defibrillation electrode resistance $R_{defib}$.

The duration of pulse T1, the magnitude of the current I1 from current source 16 and the surface area of the defibrillator electrodes, as represented by $R_{defib}$ resistance 11, will determine the threshold for electrical stimulation of the myocardium. The values chosen are subthreshold for acute pacing electrodes.

Software calibration is used to account for offset and gain errors due to amplifier offsets, charge injection, and the like.

A defibrillating device in accordance with this invention may obtain a single measurement, for example prior to delivery of a defibrillation shock. In an alternative embodiment of the invention, or as a programmable option within the device, a continuous measure of the defibrillation electrode resistance is obtained by performing the measurement at intervals of 50 ms, or another programmed interval.

The method of measuring defibrillation electrode resistance according to the invention has an application in both external and implantable defibrillating devices. Furthermore, the terms "defibrillating" and "defibrillation" may be replaced by the terms "cardioverting" and "cardioversion", as the invention is equally applicable in that case. Also, the invention has comparable application in combined pacemaker and defibrillator devices which operate automatically and include the provision of a manual programmer, as described in the aforesaid U.S. Pat. No. 4,869,252 of Norma Louise Gilli. The manual programmer may be used at any time by the patient's physician to take a reading of the defibrillation electrode resistance.

The invention is of great value at the time of implantation of an implantable defibrillator or combined pacemaker and defibrillator, as described earlier. In existing devices a defibrillation shock is required in order to measure the defibrillation electrode resistance. However, it is desirable as much as possible to prevent unnecessary defibrillation shocks to a patient. This applies especially in the situation where the defibrillation electrodes or "patches" are not correctly positioned or aligned. In this situation any unnecessary, misaligned, defibrillation shock could be extremely hazardous to the patient. Therefore a subthreshold measurement is safe not only because of the low level instantaneous current pulse, of the order of 2 mA, but because it is a safe technique since it detects the integrity of the electrodes and their positioning, based on the resistance increases that accompany a misaligned pair of electrodes.

The measurement of defibrillation resistance also has advantages subsequent to implantation and prior to the application any defibrillation therapy to be delivered to a patient as the result of detecting, and in some devices reconfirming, a tachyarrhythmia. Any variations to the integrity of the electrodes or to their positioning will be detected by this simple, almost instantaneous method which at the same time does not result in unnecessary stimulation of the patient's heart.

An instantaneous subthreshold measurement following the detection of a tachyarrhythmia in a patient provides a very useful parameter for the control of defibrillation threshold tracking. Thus, the defibrillation electrode resistance is measured prior to a defibrillation shock being delivered, and if the measurement exceeds the last measured value or a standard or average value by a specified amount, then the energy level of the defibrillation shock is adjusted to a maximum value.

The measurement further provides a means of maintaining a constant-energy defibrillation shock delivery system, especially in an implantable defibrillator. In some devices a variation in the defibrillation electrode resistance will also mean that there will be variation in the energy level of the defibrillation shock delivered. Thus, an increase in the resistance will result in a defibrillation shock of lower magnitude than the programmed energy level to be delivered. Similarly, a decrease in the defibrillation electrode resistance will result in a defibrillation shock of higher magnitude than the programmed energy level.

In either situation the patient is not receiving what he is "expecting" to receive. If the magnitude of the defibrillation shock is too low, it may be insufficient to revert the tachyarrhythmia. If the magnitude of the defibrillation shock is too high, it can be hazardous to the patient. It is desirable, therefore, to provide a constant energy defibrillation shock delivery system, to insure that the correct programmed energy level of the defibrillation shock will actually be delivered to the patient as therapy. This is achieved by an instantaneous subthreshold defibrillation electrode resistance measurement following detection of a tachyarrhythmia. Using the measured resistance value to detect any variations in the electrode resistance, the magnitude of the defibrillation shock to be delivered may be varied, i.e., increased or decreased in order to ensure that the patient actually receives the correct programmed energy level of defibrillation shock as therapy.

Based on the performance of a subthreshold defibrillation resistance measurement prior to shock, there are two algorithms that may be utilized in this invention to deliver a constant energy defibrillation shock.

These algorithms cannot be used accurately in implantable defibrillators which measure defibrillation electrode resistance at the time that a defibrillation shock is being delivered, i.e., by the "non"-subthreshold method. This is due to the fact that the measurement could easily become outdated since the time of the last defibrillation shock due to variations in load resistance.

The first algorithm, shown in FIG. 4A, maintains constant energy in the defibrillation shock by varying the duration of the shock. The defibrillation electrode resistance is measured as described above, at block 50, prior to the delivery of a defibrillation shock. Then, utilizing a programmed constant energy value obtained at block 52 and a programmed leading edge voltage obtained at block 54, the required defibrillation shock duration is calculated at block 56 and the shock is delivered at block 58. Therefore, the leading edge voltage of each defibrillation shock remains constant and the duration of the shock is varied with the changing load resistance in order to maintain a constant energy.

In an alternative method, a second algorithm, shown in FIG. 4B, maintains constant energy in the defibrillation shock by varying the leading edge voltage of the shock. The defibrillation electrode resistance is measured as described above, at block 60, prior to the delivery of the defibrillation shock. Then, utilizing a programmed constant energy value obtained at block 62 and a programmed shock duration obtained at block 64, the required leading edge voltage is calculated at block 66 and the shock is delivered at block 68. Therefore, the duration of each defibrillation shock remains constant and the leading edge voltage is varied with the changing load resistance in order to maintain a constant energy.

As indicated earlier herein, the actual energy (E) in joules delivered by a particular defibrillating device is determined by the leading edge voltage (V), the defibrillation shock duration (t), the defibrillation patch electrode resistance (R) and the defibrillator capacitance (C) in accordance with the following equation:

$$E = \tfrac{1}{2} CV^2 [1 - e^{-2t/RC}]$$

In the first constant energy shock delivery algorithm of FIG. 4A, (E) and (V) are programmable and predetermined. Immediately prior to the delivery of a shock, the defibrillation patch electrode resistance (R) is measured using the method described. These values are then substituted into the above equation, together with the value (C) of the shock delivery capacitor that is incorporated in the defibrillator circuitry, and the duration (t) of the shock is calculated. As an example of the operation of the first algorithm, it is assumed that an idealized shock delivery circuit is employed which delivers a shock from a 150 microfarad (C) capacitor with no series resistance other than the defibrillation patch electrode resistance, and that a 30 joule (J) shock with a leading edge voltage of 650 volts (V) is programmed to be utilized. Immediately before delivery of the shock, the defibrillation patch electrode resistance (R) is measured. Assuming the measured value of the defibrillation patch electrode resistance is, say, 45 ohms, this value is substituted for (R) in the above equation and the equation is solved for (t). In this example (t) equals 9.9 milliseconds. Other measured values of (R) will, of course, give different values of (t).

In the constant energy shock delivery algorithm of FIG. 4B, (E) and (t) are programmable and predetermined. Immediately prior to delivery of a shock, (R) is measured using the method described. These values are then substituted into the foregoing equation, together with the value (C) of the shock delivery capacitor, and the leading edge voltage (V) is calculated. As an example of the operation of the second algorithm, it is assumed that an idealized shock delivery circuit is employed which delivers a shock from a 150 microfarad (C) capacitor with no series resistance other than the defibrillation patch electrode resistance (R), and that a 30 joule (E) shock having a duration of 8 milliseconds (t) is programmed to be utilized. Immediately before delivery of the shock, the defibrillation patch electrode resistance (R) is measured. Assuming the measured value of the defibrillation patch electrode resistance is, say, 46 ohms, this value is substituted for (R) in the foregoing equation and the equation is solved for (V). In this example, (V) equals 666 volts. Other measured values will, of course, give different values of (V).

It will be apparent from the foregoing description that this invention provides an improved method and device wherein the integrity of defibrillation electrodes is ensured prior to delivering a defibrillation shock to a patient. The method and device perform a simple, substantially instantaneous, defibrillation electrode resistance measurement using a subthreshold technique which does not affect the electrical timing of the heart, and thereby reduces the risk to the patient. The method and device may selectively take single measurements, such as prior to the delivery of a defibrillation shock, or continually take measurements at pre-programmed intervals. In addition, the method and device provide for and control an improved constant-energy delivery system in an implantable defibrillator. They also provide a parameter for the control of threshold tracking While particular embodiments of this invention have been shown and described, it will be obvious to those skilled in the art that various other changes and modifications may be made without departing from the invention in its broader aspects, and it is, therefore, aimed in the appended claims to cover all such changes and modifications as fall within the true spirit and scope of this invention.

What is claimed is:

1. A method of controlling defibrillator operation including the step of measuring subthreshold defibrillation electrode resistance between two or more defibrillation electrodes, said measuring step further comprising the steps of sourcing a single subthreshold current pulse of predetermined magnitude across said electrodes, sampling the resulting voltage drop across said electrodes, subtracting low frequency noise and electrode polarization voltage artifacts from said resulting voltage drop to derive a defibrillation electrode voltage drop, measuring the voltage of said defibrillation electrode voltage drop, and calculating said resistance from said measured voltage and said predetermined magnitude of said current pulse.

2. A method according to claim 1, further including the step of repeating the sourcing, sampling, subtracting, measuring and calculating steps at regular intervals.

3. A method according to claim 2, wherein said regular intervals are programmable values.

4. A method according to claim 1, including the further steps of detecting a tachyarrhythmia in the patient and delivering defibrillation therapy to the defibrillation electrodes, and wherein said electrodes are implanted in a patient's body and said sourcing, sampling, subtracting, measuring and calculating steps are performed after detecting a tachyarrhythmia but prior to delivery of a defibrillation shock through the electrodes to revert said tachyarrhythmia.

5. A method according to claim 3, including the further steps of detecting a tachyarrhythmia in the patient and delivering defibrillation therapy to the defibrillation electrodes, and wherein said sourcing, sampling, subtracting, measuring and calculating steps are performed after detecting a tachyarrhythmia but prior to delivery of a defibrillation shock through the electrodes to revert said tachyarrhythmia.

6. A method according to any one of claims 1-5, said sampling step further including the sub-step of sampling said resulting voltage on a first capacitor.

7. A method according to claim 6, wherein said resulting voltage is measured by means of an analog-to-digital converter.

8. A method according to claim 6, said subtracting step further including the sub-steps of removing said current pulse and further sampling the resulting voltage on a second capacitor for the purpose of rejecting said low frequency noise and other electrode polarization voltage artifacts.

9. A method according to claim 8, wherein said sampled resulting voltage on said second capacitor is measured by means of an analog-to-digital converter.

10. A method according to claim 8, wherein the number of said defibrillator electrodes is 2.

11. A method according to anyone of claims 1-3, wherein the said defibrillator electrodes are implanted in a patient's body.

12. A method according to anyone of claims 1-3, wherein said defibrillator electrodes are positioned on an external surface of a patient's body.

13. A method according to claim 12, said sampling step further including the sub-step of sampling said resulting voltage on a first capacitor.

14. A method according to claim 13, said subtracting step further including the sub-steps of removing said current pulse and further sampling the resulting voltage on a second capacitor for the purpose of rejecting said low frequency noise and other electrode polarization voltage artifacts.

15. A method according to claim 14, wherein said sampled resulting voltage on said second capacitor is measured by means of an analog-to-digital-converter.

16. A method according to claim 15, wherein said defibrillation electrode resistance is measured between only two defibrillator electrodes.

17. A method of providing a constant-energy defibrillation shock through two or more defibrillating electrodes, comprising the steps of detecting a tachyarrhythmia, sourcing a single subthreshold current pulse across said electrodes, measuring the resulting voltage, calculating the electrode resistance from the measured voltage and the current pulse magnitude, using said calculated electrode resistance to adjust the energy level of the defibrillation shock, and delivering said energy-level-adjusted defibrillation shock through said electrodes to treat said detected tachyarrhythmia.

18. A method of providing a constant-energy defibrillation shock through two or more defibrillating electrodes, comprising the steps of detecting a tachyarrhythmia, sourcing a single subthreshold current pulse across said electrodes, measuring the resulting voltage, calculating the electrode resistance from the measured voltage and the current pulse magnitude, using the calculated electrode resistance and a predetermined leading edge voltage to calculate and adjust the duration of the defibrillation shock, and delivering a defibrillation shock through said electrodes to treat said detected tachyarrhythmia.

19. A method of providing a constant-energy defibrillation shock through two or more defibrillating electrodes, comprising the steps of detecting a tachyarrhythmia, sourcing a single subthreshold current pulse across said electrodes, measuring the resulting voltage, calculating the electrode resistance from the measured voltage and the current pulse magnitude, using the calculated electrode resistance and a predetermined shock duration to adjust the leading edge voltage of the defibrillation shock, and delivering a defibrillation shock through said electrodes to treat said detected tachyarrhythmia.

20. A method of providing a parameter for the control of defibrillation threshold tracking utilizing two or more defibrillating electrodes, comprising the steps of detecting a tachyarrhythmia, sourcing a single subthreshold current pulse across said electrodes, measuring the resulting voltage, calculating the electrode resistance from said measured voltage and the magnitude of said current pulse, comparing said calculated electrode resistance with the last resistance value so-calculated, adjusting the energy level of the defibrillation shock to a maximum value if said last resistance value is exceeded by a specified amount, and delivering said maximum defibrillation shock through said electrodes to treat said detected tachyarrhythmia.

21. A method according to any one of claims 17-20, further including the step of sampling said resulting voltage on a first capacitor in said resistance measuring circuit.

22. A method according to claim 21, wherein said resulting voltage is measured by means of an anolog-to-digital converter.

23. A method according to claim 21, further including the step of removing said current pulse and further sampling the resulting voltage on a second capacitor for the purpose of rejecting low frequency noise and other electrode polarization voltage artifacts.

24. A method according to claim 23, wherein said sampled resulting voltage on said second capacitor is measured by means of an analog-to-digital converter.

25. A method according to claim 23, wherein the number of said defibrillating electrodes is 2.

26. A method according to any one of claims 17-20, wherein said defibrillating electrodes are implanted in a patient's body.

27. A method according to any one of claims 17-20, wherein said defibrillating electrodes are positioned on an external surface of a patient's body.

28. A method according to any one of claims 17-20, including the further step of reconfirming the presence of said detected tachyarrhythmia before delivering said defibrillation shock.

29. A defibrillation device for reverting tachyarrhythmia in a patient's heart, said device including means for detecting a tachyarrhythmia condition in the heart, and means including two or more defibrillation electrodes and a source of defibrillation shock voltage for delivering defibrillation shock therapy through said electrodes to the heart, said device further including circuitry for measuring the resistance between said defibrillation electrodes, comprising:

means independent of said defibrillation shock voltage and adapted to be coupled to said defibrillation electrodes for a first predetermined period of time for sourcing a single subthreshold current pulse of predetermined magnitude across said electrodes during said predetermined period of time;

means adapted to be coupled to said electrodes for sampling the resultant voltage drop across the electrodes;

means for subtracting low frequency noise and electrode polarization artifacts from said resulting voltage drop to derive a defibrillation electrode voltage drop;

means for measuring the voltage of said defibrillation electrode voltage drop; and, means for calculating said resistance from said measured voltage and said current pulse magnitude.

30. A defibrillation device for providing a constant-energy defibrillation shock to revert tachyarrhythmia in a patient's heart, said device including means for detecting a tachyarrhythmia condition in the heart, means including two or more defibrillation electrodes and a source of defibrillation shock voltage for delivering defibrillation shock therapy through said electrodes to the heart, and a circuit for measuring the resistance between said defibrillation electrodes, said device further comprising:

means for switching said defibrillation electrodes into communication with said resistance measuring circuit;

means operative during a first predetermined time period for sourcing a single subthreshold current pulse of predetermined magnitude from said resistance measuring circuit across said electrodes;

means for measuring the resultant voltage drop;

means for calculating the defibrillation electrode resistance from the measured voltage drop and the current pulse magnitude; and, means responsive to said calculated electrode resistance and operative to adjust the energy-level of said defibrillation shock for delivering said energy-level-adjusted defibrillation shock through said electrodes to treat said tachyarrhythmia.

31. A defibrillation device for providing a constant-energy defibrillation shock to revert tachyarrhythmia in a patient's heart, said device including means for detecting a tachyarrhythmia condition in the heart, means including two or more defibrillation electrodes and a source of defibrillation shock voltage for delivering defibrillation shock therapy through said electrodes to the heart, and a circuit for measuring the resistance between said defibrillation electrodes, said device further comprising:

means for switching said defibrillation electrodes into communication with said resistance measuring circuit;

means operative during a first predetermined time period for sourcing a single subthreshold current pulse of predetermined magnitude from said resistance measuring circuit across said electrodes;

means for measuring the resultant voltage drop;

means for calculating the defibrillation electrode resistance from the measured voltage drop and the current pulse magnitude; and, means responsive to said calculated electrode resistance and to a predetermined leading edge voltage of said defibrillation shock, and operative to calculate and adjust the duration of said defibrillation shock, for delivering said duration-adjusted defibrillation shock through said electrodes to treat said detected tachyarrhtyhmia.

32. A defibrillation device for providing a constant-energy defibrillation shock to revert tachyarrhythmia in a patient's heart, said device including means for detecting a tachyarrhythmia condition in the heart, means including two or more defibrillation electrodes and a source of defibrillation shock voltage for delivering defibrillation shock therapy through said electrodes to the heart, and a circuit for measuring the resistance between said defibrillation electrodes, said device further comprising:

means for switching said defibrillation electrodes into communication with said resistance measuring circuit;

means operative during a first predetermined time period for sourcing a single subthreshold current pulse of predetermined magnitude from said resistance measuring circuit across said electrodes;

means for measuring the resultant voltage drop;

means for calculating the defibrillation electrode resistance from the measured voltage drop and the current pulse magnitude; and, means responsive to said calculated electrode resistance and to a predetermined defibrillation shock duration, and operative to adjust the leading edge voltage of said defibrillation shock, for delivering said leading-edge-voltage-adjusted defibrillation shock through said electrodes to treat said detected tachyarrhythmia.

33. A device for providing a defibrillation shock to revert tachyarrhythmia in a patient's heart, said device having a parameter for the control of defibrillation threshold tracking, and including means for detecting a tachyarrhythmia condition in the heart, means including two or more defibrillation electrodes and a source of defibrillation shock voltage for delivering defibrillation shock therapy through said electrodes to the heart, and a circuit for measuring the resistance between said defibrillation electrodes, said device further comprising:

means for switching said defibrillation electrodes into communication with said resistance measuring circuit;

means operative during a first predetermined time period for sourcing a single subthreshold current pulse of predetermined magnitude from said resistance measuring circuit across said electrodes, means for measuring the resultant voltage drop;

means for calculating the defibrillation electrode resistance from the measured voltage drop and the current pulse magnitude;

means for comparing the calculated electrode resistance to the last resistance value so-calculated; and, means responsive to said comparison and operative to adjust the energy level of the defibrillation shock to a maximum value when said calculated resistance exceeds by a predetermined amount said last resistance value so-calculated, for delivering said maximum defibrillation shock through said electrodes to treat said detected tachyarrhythmia.

34. A device according to any one of claim 29-33, further including means operative after said defibrillation electrodes resistance has been calculated and before the delivery of said defibrillation shock for reconfirming the presence of said detected tachyarrhythmia and cancelling said defibrillation shock delivery in the absence of such confirmation.

35. A device according to any one of claims 29-33 wherein said means for measuring the resultant voltage drop includes a first capacitor coupled to said electrodes for sampling the voltage across said electrodes during said predetermined time.

36. A device according to claim 35, wherein said resistance measuring circuitry further includes an analog-to-digital converter coupled to said first capacitor for measuring the voltage sampled by said first capacitor.

37. A device according to claim 35, wherein said means for measuring the resultant voltage drop further includes a second capacitor coupled to said first capacitor and said electrodes during a second predetermined time following said first predetermined time period for sampling said resultant voltage drop on said second capacitor, said means for measuring the resultant voltage drop being constructed and arranged to provide for rejection of low frequency noise and electrode polarization voltage artifacts from the voltage appearing on said second capacitor.

38. A device according to claim 37, further including means operative after said defibrillation electrode resistance has been calculated and before the delivery of said defibrillation shock for reconfirming the presence of said detected tachyarrhythmia and cancelling said defibrillation shock delivery in the absence of such confirmation.

39. A device according to claim 37, wherein said resistance measuring circuitry further includes an analog-to-digital converter coupled to said second capacitor for measuring the voltage sampled by said second capacitor.

40. A device according to any one of claims 29-33, further including means for detecting a bradycardia condition in the heart and means for providing bradycardia support pacing to the heart, whereby said defibrillating device is a combined pacemaker and defibrillator.

41. A device according to claim 40, further including means for manually and automatically programming said device, whereby said combined pacemaker and defibrillator is an automatic programmed device capable of being manually programmed to measure said defibrillation electrode resistance at preselected times.

42. A device according to any one of claims 29-33, wherein said defibrillation electrodes are adapted to be implanted in the patient's body.

43. A device according to any one of claims 29-33, wherein said defibrillation electrodes are adapted to be positioned on an external surface of a patient's body.

44. A device according to claim 38, wherein said defibrillation electrodes are adapted to be implanted into patient's body.

45. A device according to claim 38, wherein said defibrillation electrodes are adapted to be positioned on an external surface of a patient's body.

46. A device according to claim 41, wherein said defibrillation electrodes are adapted to be implanted into patient's body.

47. A device according to claim 41, wherein said defibrillation electrodes are adapted to be positioned on an external surface of a patient's body.

* * * * *